(12) United States Patent
Voyer et al.

(10) Patent No.: US 9,827,600 B2
(45) Date of Patent: Nov. 28, 2017

(54) MOVABLE RACK ASSEMBLY WITH CORNER SPRAY NOZZLES

(71) Applicant: STERIS Inc., Temecula, CA (US)

(72) Inventors: Guillaume Voyer, Quebec (CA); Ghislain Parent, Saint Isidore (CA)

(73) Assignee: STERIS INC., Temecula, CA (US)

( * ) Notice: Subject to any disclaimer, the term of this patent is extended or adjusted under 35 U.S.C. 154(b) by 170 days.

(21) Appl. No.: 14/603,542

(22) Filed: Jan. 23, 2015

(65) Prior Publication Data

US 2015/0239018 A1  Aug. 27, 2015

Related U.S. Application Data

(60) Provisional application No. 61/945,441, filed on Feb. 27, 2014.

(51) Int. Cl.
| | | |
|---|---|---|
| *B08B 3/02* | (2006.01) | |
| *B05B 13/04* | (2006.01) | |
| *B05B 3/04* | (2006.01) | |
| *A47L 15/14* | (2006.01) | |
| *A61L 2/18* | (2006.01) | |

(52) U.S. Cl.
CPC .............. *B08B 3/024* (2013.01); *A47L 15/14* (2013.01); *A61L 2/18* (2013.01); *B05B 3/0409* (2013.01); *B05B 13/0421* (2013.01)

(58) Field of Classification Search
CPC . B08B 3/024; A47L 15/14; A61L 2/00; A61L 2/18; B05B 3/0409; B05B 13/0421
USPC ......................................................... 134/198
See application file for complete search history.

(56) References Cited

U.S. PATENT DOCUMENTS

| | | | |
|---|---|---|---|
| 2,336,402 A | 12/1943 | Kaiser | 4/152 |
| 3,391,409 A | 7/1968 | Gatley | 4/151 |
| 4,993,444 A | 2/1991 | Toriyama et al. | 134/181 |
| 5,488,965 A | 2/1996 | Hori | 134/180 |
| 5,749,385 A | 5/1998 | Rochette et al. | 134/199 |
| 6,869,029 B2 | 3/2005 | Ochoa, Sr. et al. | 239/380 |

(Continued)

OTHER PUBLICATIONS

International Search Report and Written Opinion (English version only) from corresponding PCT/US2015/012819 (Forms PCT/ISA/210 and PCT/ISA/237); 8 pages, dated May 4, 2015.

(Continued)

*Primary Examiner* — Michael Barr
*Assistant Examiner* — Tinsae Ayalew
(74) *Attorney, Agent, or Firm* — Kusner & Jaffe (57) ABSTRACT

A movable rack assembly for a washer having a generally rectangular frame. The frame includes a central hub connectable to a fluid source. A plurality of elongated tubular base members extends from the central hub and defines a bottom of the frame. A pair of spaced-apart elongated, tubular side members defines side portions of the frame and a space therebetween. Each of a plurality of spaced-apart transverse members has ends that are connected to one of the side members. The transverse members transverse the space defined between the side members. A rotary spray arm is attached to each of the transverse members. A plurality of corner spray nozzles on the frame directs fluid toward corners of the frame. The bottom members, the side members and the transverse members are fluidly connected with each other and fluidly connect the rotary spray arms and the corner spray nozzles with the central hub.

20 Claims, 6 Drawing Sheets

(56) References Cited

U.S. PATENT DOCUMENTS

| | | |
|---|---|---|
| 7,314,238 B2 | 1/2008 | Robert .................... 285/103 |
| 7,896,977 B2 | 3/2011 | Gillum et al. ................ 134/56 |
| 8,113,222 B2 | 2/2012 | Bertsch et al. .............. 134/181 |
| 8,211,243 B2 | 7/2012 | Delgado ...................... 134/56 |
| 8,282,741 B2 | 10/2012 | Bertsch et al. ................ 134/18 |
| 8,333,207 B2 | 12/2012 | Calhoun et al. .............. 134/172 |
| 2003/0163867 A1 | 9/2003 | Zhou ............................... 4/599 |
| 2006/0178246 A1* | 8/2006 | Tjerrild .................. F16L 3/133 |
| | | 482/24 |
| 2011/0146734 A1 | 6/2011 | Rappette ...................... 134/198 |
| 2012/0279535 A1 | 11/2012 | Robert et al. ................ 134/198 |
| 2012/0285491 A1 | 11/2012 | Blanchard et al. .......... 134/25.2 |
| 2013/0062300 A1* | 3/2013 | Drake ................... A47B 57/34 |
| | | 211/183 |

OTHER PUBLICATIONS

Examination Report issued in corresponding Australian Patent Application No. 2015223488 dated Apr. 17, 2017.
Examiner's Requisition issued in corresponding Canadian Patent Application No. 2,936,931 dated Jun. 21, 2017.

* cited by examiner

MOVABLE RACK ASSEMBLY WITH CORNER SPRAY NOZZLES

RELATED APPLICATIONS

This application claims the benefit of U.S. Provisional Application No. 61/945,441 filed Feb. 27, 2014, which is hereby fully incorporated herein by reference.

FIELD OF THE INVENTION

The present invention relates generally to the art of cleaning and decontamination, and more particularly, to an apparatus for use in a decontamination unit (washer). It will be understood, however, that the disclosed apparatus may be used in other systems wherein a fluid is sprayed.

BACKGROUND OF THE INVENTION

Decontamination units (washers) include a washing chamber wherein articles or equipment to be cleaned are placed. Conventional decontamination units (washers) include racks for holding the articles or equipment. Rotary spray arms are mounted to the racks to spray a washing fluid on the articles or equipment. Conventionally, these rotary spray arms generate a generally conical spray pattern. However, such a spray pattern may miss articles or equipment that is placed in the corner of the washing chamber. The inadequate coverage reduces the overall washing performance of the decontamination unit (washer), often resulting in longer cycle times.

Moreover, due to the need to decontaminate larger loads, decontamination units (washers) are being designed with larger washing chambers. However, these larger washing chambers often have even larger corners. In some instances, only the length of the washing chamber is increased, thereby causing the washing chamber to be more rectangular in shape. The rectangular shape of the washing chamber makes it even more difficult to have adequate coverage and impingement of the washing fluid in the corners of the washing chamber when only conventional rotating spray arms are used.

The present invention overcomes these and other problems and provides a movable rack assembly having a tubular frame that acts as a manifold for conveying fluid to nozzles disposed in corners of the movable rack assembly. As such, the present invention provides an apparatus with improved washing efficiency, as compared to rack assemblies known heretofore.

SUMMARY OF THE INVENTION

In accordance with a preferred embodiment of the present invention, there is provided a movable rack assembly for a washer having a generally rectangular frame. The frame includes a central hub connectable to a fluid source. A plurality of elongated tubular base members extends from the central hub. The base members define a bottom portion of the frame. A pair of spaced-apart elongated, tubular side members defines side portions of the frame. The side members lie in planes that are generally parallel to each other to define a space therebetween. The side members have distal ends wherein each distal end is connected to an end of one of the base members. A plurality of spaced-apart transverse members each has an end that is connected to one of the side members. The transverse members transverse the space defined between the side members. A rotary spray arm is attached to each of the transverse members. A plurality of corner spray nozzles on the frame directs fluid toward corners of the frame. The bottom members, the side members and the transverse members are fluidly connected with each other and fluidly connect the rotary spray arms and the corner spray nozzles with the central hub.

In accordance with another embodiment of the present invention, there is provided a movable rack assembly for a washer. The movable rack assembly includes a generally rectangular frame. The frame includes a central hub connectable to a fluid source. A plurality of elongated tubular base members extends from the central hub. The base member defines a bottom portion of the frame. A vertical member extends upwardly from a distal end of each of the plurality of elongated tubular base members. The vertical members and the base members define an interior space of the frame. A plurality of spaced-apart transverse members has ends connected respectively to the vertical members. The transverse members transverse the interior space of the frame. A rotary spray arm is attached to each of the transverse members. A plurality of corner spray nozzles on the frame directs fluid toward corners of the frame. The bottom members, the vertical members and the traversing members are fluidly connected with each other and fluidly connect the rotary spray arms and the corner spray nozzles with the central hub.

An advantage of the present invention is the provision of a movable rack assembly for distributing a washing fluid in a chamber of a decontamination unit (washer).

Another advantage of the present invention is an apparatus as described above that provides for improved coverage of the washing fluid in corners of the chamber of the decontamination unit (washer).

A still further advantage of the present invention is an apparatus as described above that provides for improve impingement of the washing fluid on objects disposed in the corners of the chamber of the decontamination unit (washer).

Another advantage of the present invention is an apparatus as described above wherein a frame of the movable rack assembly acts as a manifold for distributing the washing fluid throughout the washing chamber of the decontamination unit (washer).

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
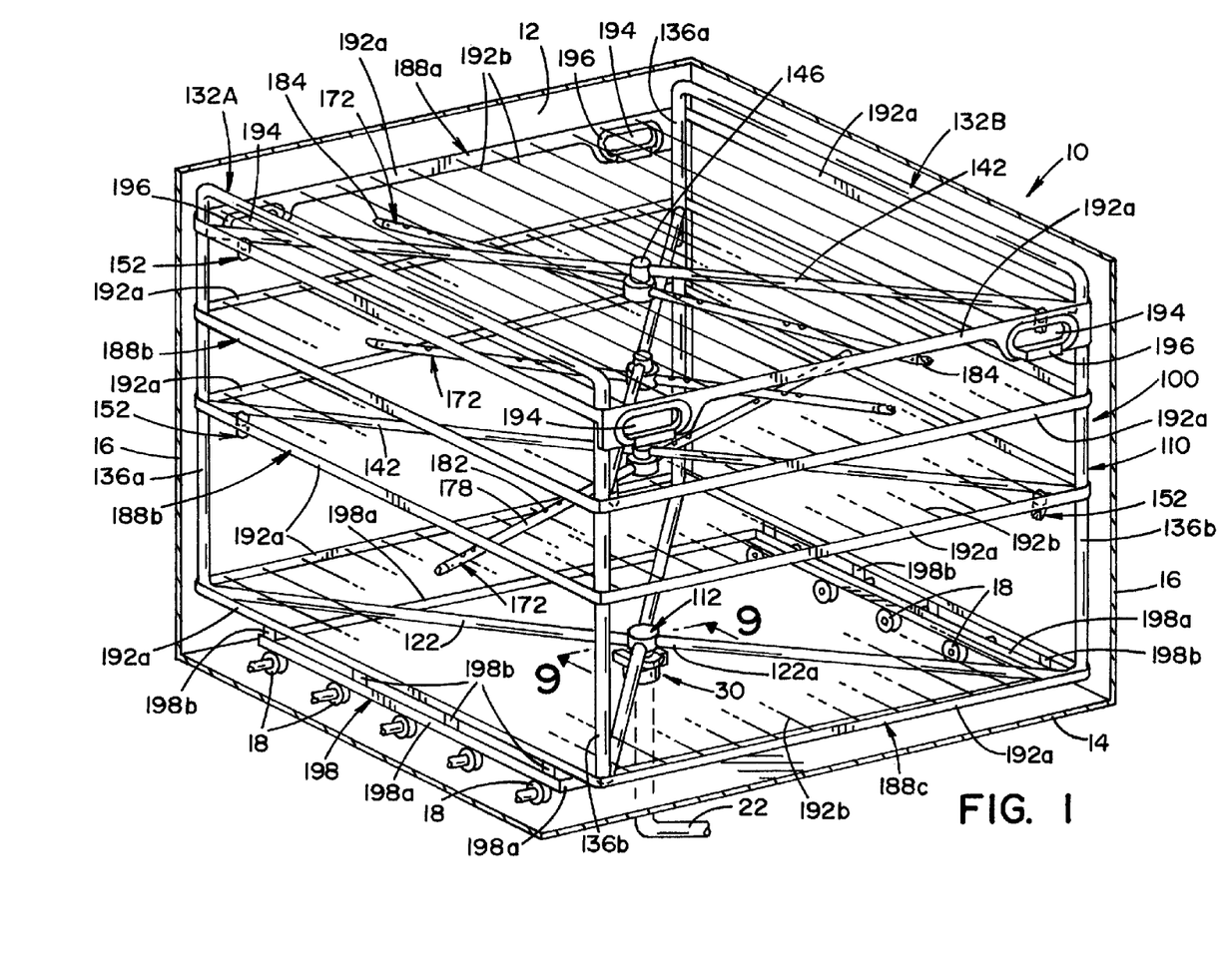
FIG. 1 is a partially sectioned, perspective view of a decontamination unit (washer) showing a movable rack assembly disposed within a washing chamber of the decontamination unit (washer)

Referring now to the drawings wherein the showings are for the purpose of illustrating a preferred embodiment of the invention only and not for the purpose of limiting same, FIG. 1 shows a movable rack assembly 100 disposed within a chamber 12 of a decontamination unit (washer) 10, illustrating a preferred embodiment of the present invention.

Decontamination unit (washer) 10 is generally rectangular in shape and includes a top wall (not shown), a bottom wall 14 and side walls 16 that define chamber 12. A door (not shown) is provided for allowing movable rack assembly 100 to be inserted into and removed from chamber 12. A plurality of wheels 18 is disposed in chamber 12 for allowing a user to easily insert and remove movable rack assembly 100 into and from chamber 12. A stationary fluid inlet line 22 extends through bottom wall 14 and fluidly connects movable rack assembly 10 to a circulation system (not shown). A fluid connection 30, described in detail below, is attached to an end of stationary fluid inlet line 22.

Referring now to FIG. 1, movable rack assembly 100, according to the present invention, is best seen. Movable rack assembly 100 includes a frame assembly 110, a plurality of rotating spray arm assemblies 172, and a plurality of shelves 188.

Figure 2:
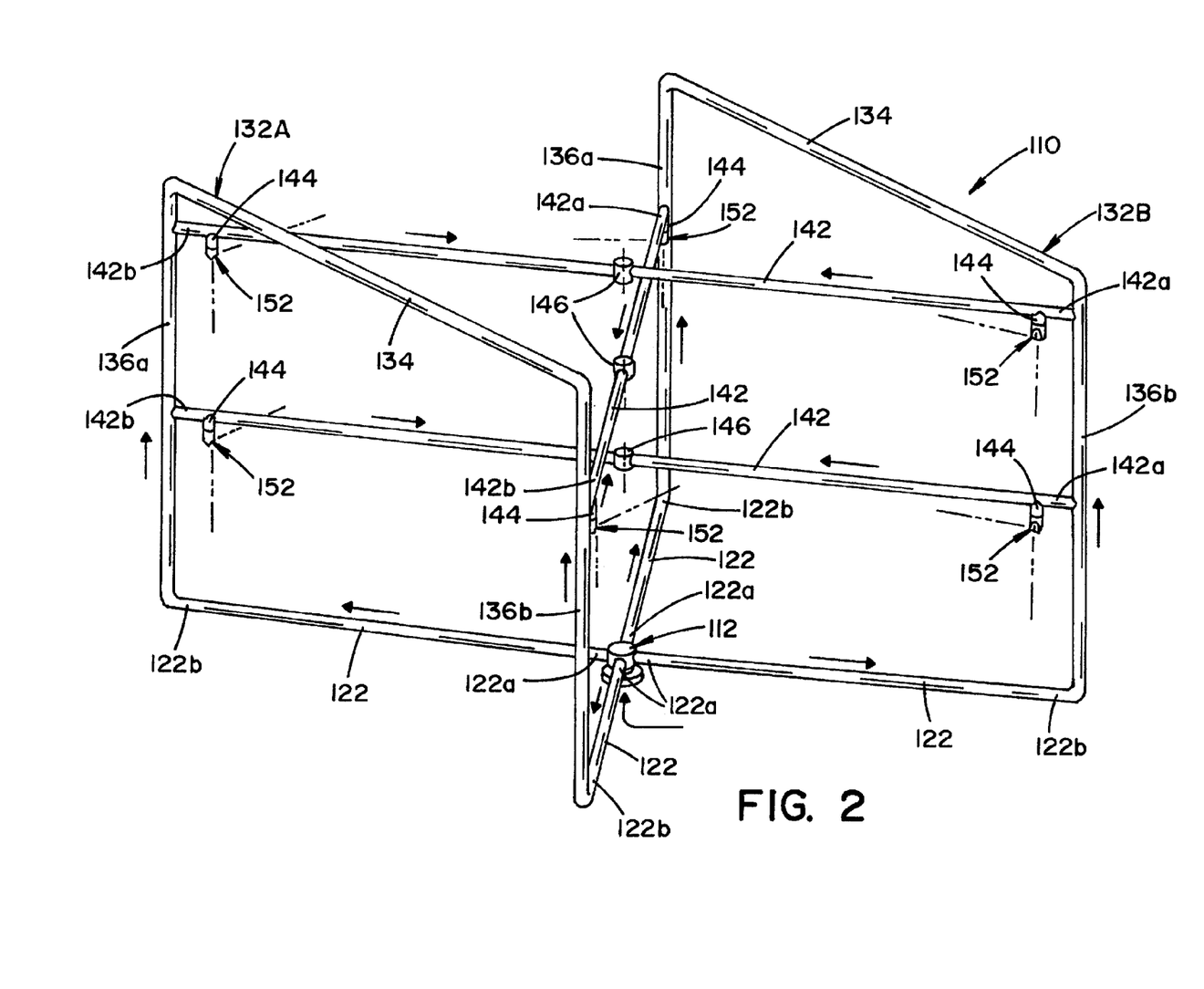
FIG. 2 is a perspective view of the movable rack assembly shown in FIG. 1, showing a frame assembly of the movable rack assembly.

Referring now to FIG. 2, frame assembly 110 is best seen. Frame assembly 110 is generally rectangular in shape. Frame assembly 110 includes a central hub 112, a plurality of tubular base members 122, two (2) U-shaped tubular frame members 132A, 132B, a plurality of tubular transverse members 142 and a plurality of corner spray nozzles 152.

Figure 9:
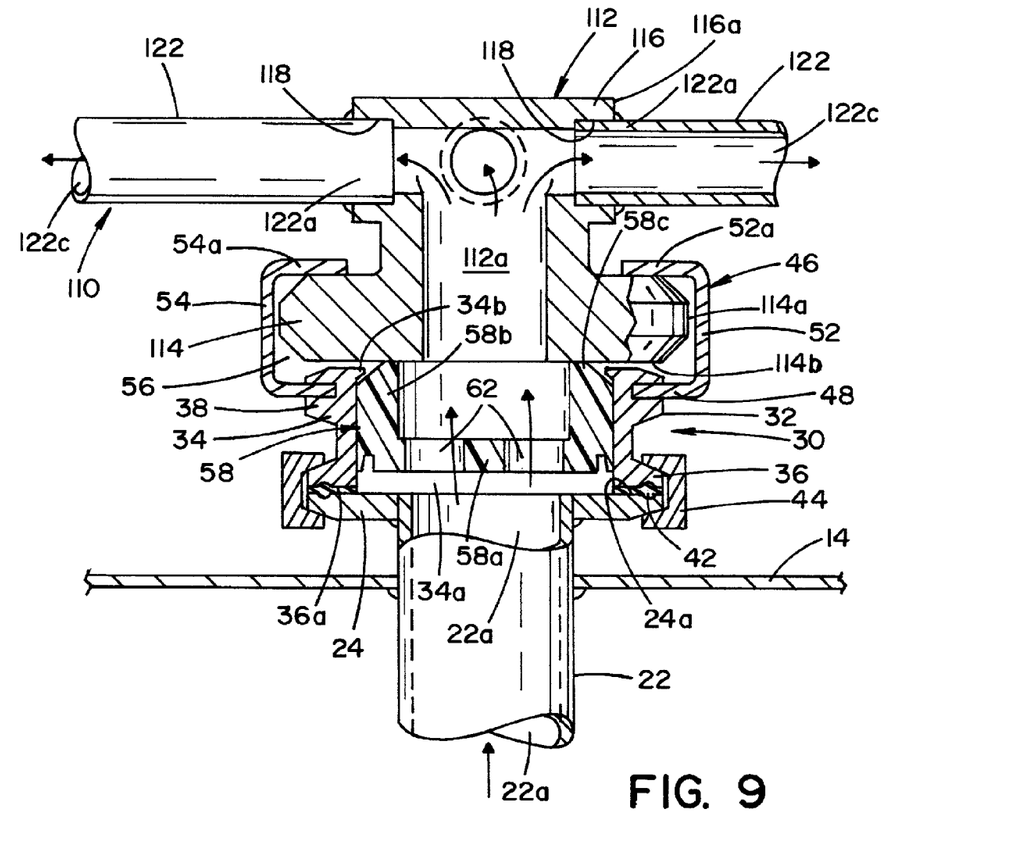
FIG. 9 is a partially sectioned, elevational view taken along line 9-9 of FIG. 1 showing the movable rack assembly connected to a fluid connection in a bottom of a chamber of the decontamination unit (washer).

Central hub 112 of frame assembly 110 fluidly connects frame assembly 110 to the circulation system of decontamination unit (washer) 10. As best seen in FIG. 9, central hub 112 is generally cylindrical shape. A first outwardly extending flange 114 is disposed at a lower end of cylindrical hub 112 and a second outwardly extending flange 116 disposed at an upper end thereof. A cylindrical cavity 112a extends axially into the lower end of central hub 112. First flange 114 has an outer edge 114a that is tapered, and a planar end surface 114b. First flange 114 is dimensioned to be disposed in registry with fluid connection 30, as described in detail below. Second flange 116 has an outer cylindrical surface 116a. Four (4) spaced-apart holes 118 extend into outer cylindrical surface 116a of second flange 116 and fluidly communicates with cylindrical cavity 112a of central hub 112. Two (2) holes are oriented toward one side of frame assembly 110 and two (2) holes are oriented toward an opposite side of frame assembly 110. In the embodiment shown, holes 118 extend in a radial direction into outer cylindrical surface 116a of second flange 116.

A tubular base member 122 is disposed in each hole 118 of central hub 112. Each tubular base member 122 has a first end 122a, a second end 122b and an internal cavity 122c extending axially between first end 122a and second end 112b. First end 122a of each tubular base member 122 is dimensioned to be disposed in one of spaced-apart hole 118. In this respect, two (2) tubular base members 122 are oriented toward one side of frame assembly 110 and two (2) tubular base members 122 are oriented toward the opposite side of frame assembly 110. As shown in FIG. 2, the four (4) tubular base members 122, in combination, define a bottom of frame assembly 110. Inner cavity 122c of each tubular base member 122 fluidly communicates with cylindrical cavity 112a of central hub 112, as best seen in FIG. 9.

Referring now to FIG. 2, two (2) U-shaped tubular frame members 132A, 132B are connected to second ends 122b of tubular base members 122. U-shaped tubular frame members 132A, 132B are identical and only U-shaped tubular frame member 132A will be described in detail below.

U-shaped tubular frame member 132A includes a horizontal base portion 134, a first vertical leg portion 136a and a second vertical leg portion 136b. A cavity extends through horizontal base portion 134, first vertical leg portion 136a and second vertical leg portion 136b. First vertical leg portion 136a and second vertical leg portion 136b each extends downwardly from an end of base portion 134.

U-shaped tubular frame member 132A is attached to two (2) tubular base members 122 that extend to one side of frame assembly 110. In particular, an end of first vertical leg portion 136a is attached to second end 122b of one tubular base member 122 that extends toward the side of frame assembly 110. An end of second vertical leg portion 136b is attached to second end 122b of tubular base member 122 that extends toward the same side of frame assembly 110. In this respect, U-shaped tubular frame member 132A defines a side of frame assembly 110. In the embodiment shown, first and second vertical leg portions 136a, 136b define vertical corners of frame assembly 110.

Similar to U-shaped tubular frame member 132A, U-shaped tubular frame member 132B is attached to the two (2) tubular base members 122 that extend to the opposite side of frame assembly 110. In the embodiment shown, U-shaped tubular frame members 132A, 132B lie in planes that are generally parallel to each other such that U-shaped tubular frame members 132A, 132B define a space of frame assembly 110 therebetween.

A plurality of spaced-apart tubular transverse members 142 extend diagonally across the space of frame assembly 110 between corners disposed on opposite sides of frame assembly 110. Each tubular transverse member 142 has a first end 142a, a second end 142b and a cavity 142c extending between first end 142a and second end 142b.

Each tubular transverse member 142 is generally parallel to the bottom of frame assembly 110. Each tubular transverse member 142 is attached to corners of frame assembly 110 such that first end 142a of each tubular transverse member 142 is attached to one of U-shaped tubular frame member 132A or U-shaped tubular frame member 132B and second end 142b of each tubular transverse member 142 is attached to the other of U-shaped tubular frame member 132A or U-shaped tubular frame member 132B. In the embodiment shown in FIG. 2, frame assembly 110 includes three (3) tubular transverse members 142, i.e., an uppermost tubular transverse member, a middle tubular transverse member and a lowermost tubular transverse member. Middle transverse member is oriented transverse to upper transverse member and lower transverse member.

Internal cavity 142c of each tubular transverse member 142 fluidly communicates with the internal cavities of U-shaped tubular frame members 132A, 132B. In this respect, base members 122, U-shaped frame members 132A, 132B and tubular transverse members 142 define fluid pathways through frame assembly 110.

Figure 4:
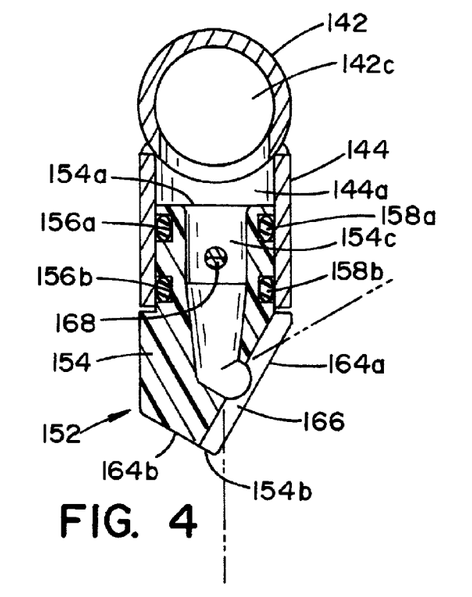
FIG. 4 is a sectioned view taken along line 4-4 of FIG. 3, showing a corner spray nozzle attached to a frame assembly of the movable rack assembly.
Figure 5:
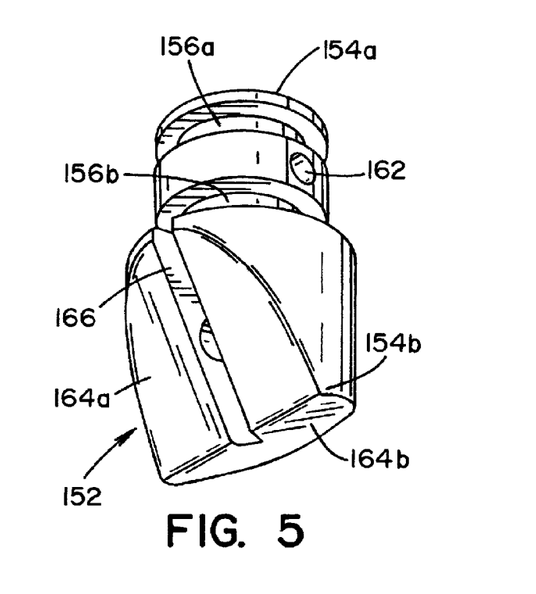
FIG. 5 is a perspective view of the corner spray nozzle shown in FIG. 4.
Figure 6:
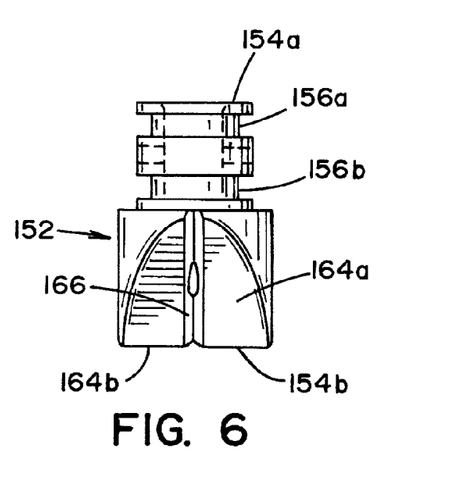
FIG. 6 is a front elevation view of the corner spray nozzle shown in FIG. 5.
Figure 7:
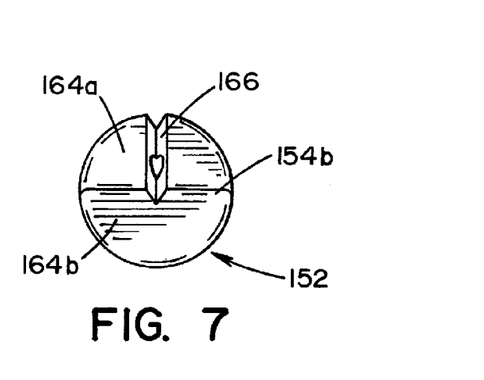
FIG. 7 is a bottom elevation view of the corner spray nozzle shown in FIG. 5.

A boss 144 is disposed near each of first end 142a and second end 142b of tubular transverse member 142. As best seen in FIG. 4, each boss 144 is a tubular element and has a cavity 144a extending therethrough. Boss 144 is attached to tubular transverse member 142 such that cavity 144a of boss 144 fluidly communicates with internal cavity 142c of tubular transverse member 142. Holes (not shown) extend through side walls of boss 144 and are positioned and dimensioned as described in detail below.

One corner spray nozzle 152 is disposed in each boss 144 of tubular transverse member 142. As best seen in FIGS. 3-7, corner spray nozzle 152 includes a nozzle body 154 having a first end 154a and a second end 154b and a cavity 154c extending axially therethrough. Two (2) spaced apart annular grooves 156a, 156b are formed in an outer surface of nozzle body near first end 142a of tubular traverse member 142. Each groove 156a, 156b is dimensioned to accept a conventional o-ring 158a, 158b for providing a seal between first end 154a of nozzle body 154 and an inner surface of boss 144 of tubular transverse member 142. Second end 142b of corner spray nozzle 152 is contoured to define two (2) sloped surfaces 164a, 164b. Sloped surface 164a intersects cavity 154c extending through nozzle body 154. A V-shaped groove 166 extends along sloped surface 164a. Groove 166 is positioned and dimensioned such that cavity 154c of nozzle body 154 communicates with a bottom of V-shaped groove 166. A hole 162 extends radially through nozzle body 154 at a location between groove 156a and groove 156b. Hole 162 is dimensioned and positioned to align with the holes in the side wall of boss 144.

Corner spray nozzle 152 is disposed within boss 144 such that hole 162 of corner spray nozzle 152 aligns with the holes in the side wall of boss 144. A pin 168 extends through the holes in boss 144 and hole 162 in corner spray nozzle 152 to secure corner spray nozzle 152 into boss 144.

As shown in FIG. 2, a spray arm mounting boss 146 is disposed between first end 142a and second end 142b of each tubular transverse member 142. Each spray arm mounting boss 146 is a tubular element having a closed upper end and a cavity (not shown) extending into a lower end thereof. Each spray arm mounting boss 146 is attached to a single tubular transverse member 142 such that the cavity formed in spray arm mounting boss 146 fluidly communicates with internal cavity 142a of the respective tubular transverse member 142.

As shown in FIG. 1, a rotatable spray arm assembly 172 is rotatably attached to each spray arm hub 146. In the embodiment shown, rack assembly 100 includes three (3) spray arm assemblies 172. Spray arm assemblies 172 are essentially identical and only one spray arm assembly 172 will be described below.

Figure 8:
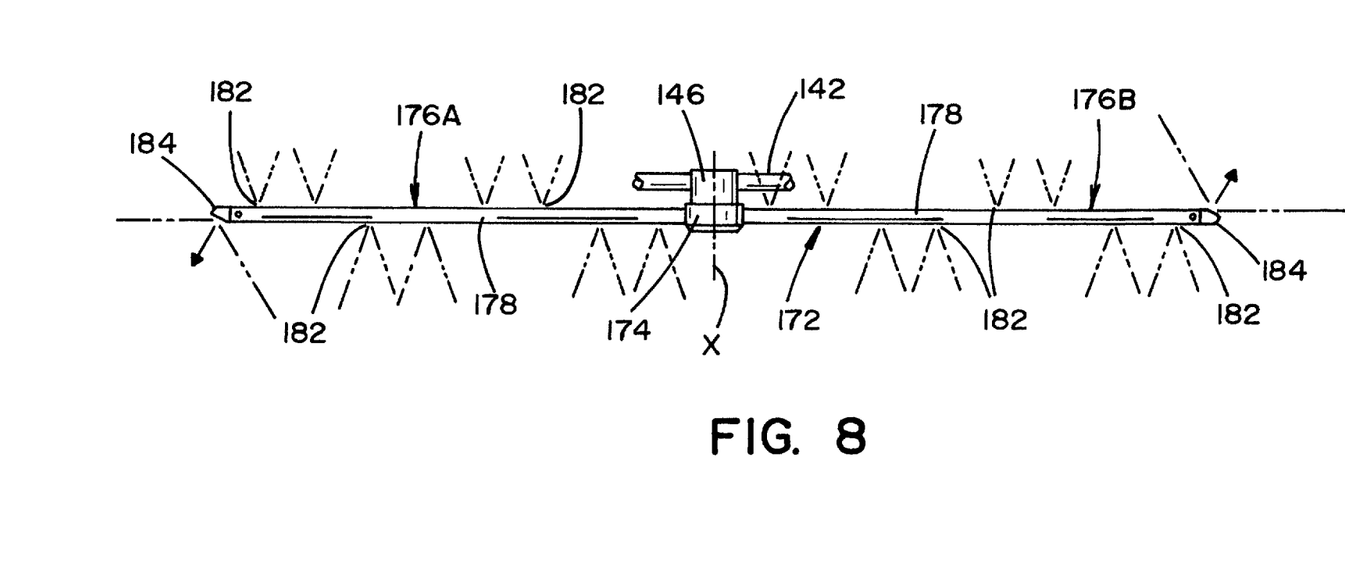
FIG. 8 is a side elevation view of a rotating spray arm assembly of the movable rack assembly shown in FIG. 1.

Referring now to FIG. 8, rotatable spray arm assembly 172 is best seen. Rotatable spray arm assembly 172 is generally comprised of a central hub 174 with arm assemblies 176A, 176B extending therefrom. Central hub 174 defines an internal cavity (not shown) that is in fluid communication with spray arm hub 146 on tubular transverse member 142. Central hub 174 is mounted to spray arm hub 146 to rotate about a fixed axis 'X.' In this respect, spray arm assembly 172 rotates about fixed axis 'X.' In the embodiment shown, spray arm assembly 172 includes two arm assemblies 176A, 176B extending from central hub 174. It is also contemplated that more than two, equally-spaced arm assemblies may extend from central hub 174.

In the embodiment shown, arm assemblies 176A, 176B are essentially identical. Accordingly, only one arm assembly 176A will be described in detail. Arm assembly 176A is generally comprised of an elongated tubular member 178. Tubular member 178 defines an internal passage (not shown) that extends a length of tubular member 178. A series of spaced-apart spray nozzles 182 extend through a wall of tubular member 178 at discrete locations along tubular member 178. In the embodiment shown, tubular member 178 is a cylindrical tube and spray nozzles 182 are openings. A spray nozzle 184 is attached to a distal end of each arm assembly 176A, 176B. Spray nozzle 184 is essentially identical to corner spray nozzle 152 and will not be described in detail.

In the embodiment shown in FIG. 1, movable rack assembly 100 includes four (4) permanent shelves, i.e., an uppermost shelf 188a, two (2) intermediate shelves 188b and a lowermost shelf 188c. Plurality of shelves 188a, 188b, 188c is attached to frame assembly 110 of movable rack assembly 100. Each shelf 188a, 188b, 188c includes elongated bar elements 192a that extend between adjacent vertical leg portions 136a, 136b of U-shaped tubular frame members 132A, 132B. A plurality of thin, rod-shaped elements 192b extends between bar-shaped elements 192a located on opposite sides of frame assembly 110 to define a surface of shelf 188a, 188b, 188c for receiving instruments (not shown) thereon.

Uppermost shelf 188a of movable rack assembly 100 includes an elongated opening 194 formed near each end of two (2) bar elements 192a of uppermost shelf 188a. In the embodiment shown, a molded rubber insert 196 is disposed in each elongate opening 194 for providing protection to a user, as explained in detail below.

A support frame 198 is attached to the bottom of movable rack assembly 100. Support frame 198 is generally rectangular in shape and includes a plurality of elongated bar elements 198a that are spaced from the bottom of movable rack assembly 100 by spacers 198b. Bar elements 198a are dimensioned and positioned to engage wheels 18 of decontamination unit (washer) 10 when movable rack assembly 100 is moved into and removed from chamber 12 of decontamination unit (washer) 10. In this respect, movable rack assembly 100 rolls on wheels 18 when movable rack assembly 100 is inserted into, and removed from, chamber 12 of decontamination unit (washer) 10.

As best seen in FIG. 9, a fluid connection 30 of decontamination unit (washer) 10 is attached to an end of stationary fluid inlet 22 to provide a fluid connection between movable rack assembly 100 and decontamination unit (washer) 10. Fluid connection 30 is described in detail in U.S. Pat. No. 7,314,238, hereby incorporated herein by reference. In generally, fluid connection 30 is basically comprised of a stationary fitting 32 for attachment to stationary fluid inlet line 22.

Stationary fitting 32 includes a piston body 34. Piston body 34 is cylindrical in shape and includes an outwardly extending annular flange 36 at one end and an outwardly extending boss or mount 38 at the other end. Flange 36 has a planar surface 36a dimensioned to mate with a planar surface 24a on a flange element 24 of stationary fluid inlet line 22. An annular seal 42 is disposed between flange 36 on piston body 34 and flange 24 on stationary fluid inlet line 22 to form a fluid seal therebetween. Flange 36 and flange element 24 are held together by a conventional collar clamp 44. Flange 36 and flange element 24 have beveled edges to matingly engage tapered inner surfaces along the inner edge of collar clamp 44.

Outwardly extending boss or mount 38 on piston body 34 has a generally C-shaped bracket 46 secured thereto. Bracket 46 has a planar base 48 and sides 52, 54 that are generally L-shaped. Sides 52, 54 have inwardly turned ends 52a, 54a. A generally rectangular slot or space 56 is formed between planar base 48, sides 52, 54 and ends 52a, 54a of C-shaped bracket 46.

Piston body 34 defines a cylindrical inner cavity 34a that communicates with opening 22a in stationary fluid inlet line 22, and that extends through C-shaped bracket 46 to communicate with rectangular slot or space 56 defined by C-shaped bracket 46. An inwardly extending lip 34b is formed at one end of piston body 34. Lip 34b is formed on the end of piston body 34 where C-shaped bracket 46 is connected to piston body 34.

Piston cavity 34a is dimensioned to receive a piston 58. Piston 58 is generally cylindrical in shape. Piston 58 may be a solid cylindrical plug, but in the embodiment shown, piston 58 is generally C-shaped. In this respect, piston 58 includes a bottom wall 58a and an annular, cylindrical side wall 58b extending to one side of bottom wall 58a. A plurality of spaced-apart apertures 62 is formed in bottom wall 58a. Apertures 62 are dimensioned such that the total cross-sectional area of all apertures 62 is less than the cross-sectional area of an opening 22a of stationary fluid inlet line 22. The free end of side wall 58b is tapered to form a conical-shaped end 58c. By way of example, and not limitation, piston 58 may be formed of teflon or stainless steel. Central hub 112 of frame assembly 100 is dimensioned to be slidably received within rectangular space 56 defined by C-shaped bracket 46 of stationary fitting 32.

Referring now to the operation of movable rack assembly 100, articles to be decontaminated are first placed on shelves 188a, 188b, 188c of movable rack assembly 100. The door of decontamination unit (washer) 10 is opened and movable rack assembly 100 is inserted into chamber 12 of decontamination unit (washer) 10. In particular, support frame 198 of movable rack assembly 100 engages wheels 18 in decontamination unit (washer) 10 to allow a user to easily insert movable rack assembly 100 into chamber 12.

As movable rack assembly 100 is inserted into chamber 12, central hub 112 connects to fluid connection 30 of decontamination unit (washer) 10. Movable rack assembly 100 is dimensioned such that when movable rack assembly 100 is fully disposed within chamber 12, central hub 112 is positioned adjacent stationary fitting 32. In particular, first flange 114 on cylindrical body 112 slides into space or slot 56 defined by C-shaped bracket 46. Central hub 112 is positioned such that cylindrical opening 112a of central hub 112 is aligned with piston cavity 34a in piston body 34. In this respect, cylindrical opening 112a of central hub 112 is basically in axial alignment with the axis of cylindrical piston 58.

During one or more phases of the operation of the decontamination unit (washer), pressurized fluid is conveyed through stationary fluid inlet line 22 into cavity 34a of piston body 34. Since apertures 62 and piston 58, in total, define a smaller, cross-sectional area than the cross-sectional area of opening 22a of stationary fluid inlet line 22, a pressure build up will occur within cavity 34a in piston body 34. The pressure on the face of bottom wall 58a of piston 58 forces piston 58 in a direction towards surface 114b of first flange 114. In this respect, conical end 58c of piston 58 is forced against surface 114b of first flange 114 forming a fluid connection therewith. As shown in FIG. 9, fluid flows through apertures 62 into cylindrical opening 112c of central hub 112. From there, pressurized fluid flows through internal cavity 122c of base tubular members 122.

Figure 3:
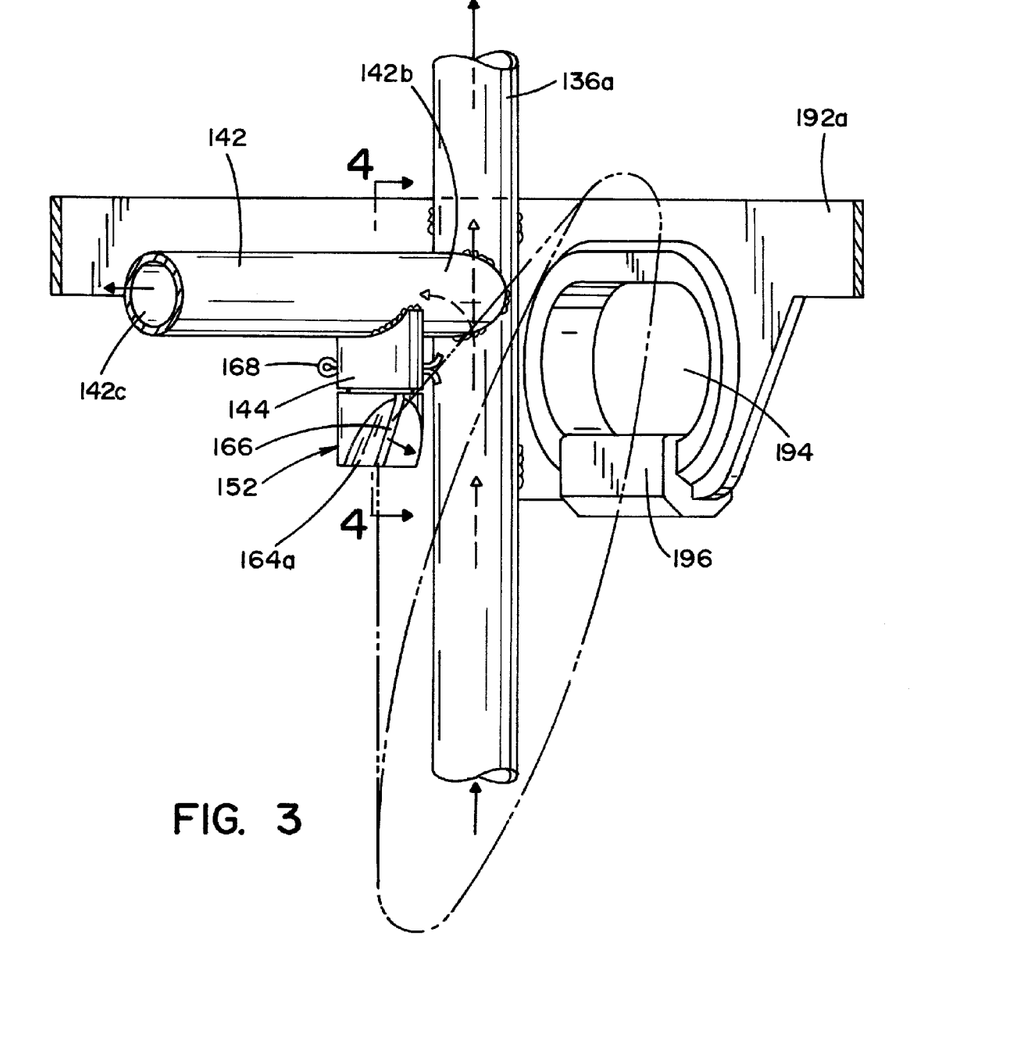
FIG. 3 is a partially sectioned, elevational view of the frame assembly shown in FIG. 2 showing a corner spray nozzle of the rack assembly.

As noted above, base members 122, U-shaped frame members 132A, 132B and tubular transverse members 142 define fluid pathways through frame assembly 110, as illustrated by arrows in FIG. 2. In particular, the fluid flowing through internal cavity 122c of base tubular members 122 is directed through the internal cavity in each U-shaped tubular assembly 132A, 132B. Each U-shaped tubular assembly 132A, 132B is fluidly connected to cavity 142c of one or more tubular transverse member 142. The fluid in cavity 142c is conveyed through boss 144 and to a respective corner spray nozzle 152. As shown in FIG. 3, fluid exiting corner spray nozzles 152 form a conical spray pattern for spraying fluid on articles disposed in the corners of movable rack assembly 100. According to the present invention, corner spray nozzles 152 are designed to provide improve impingement of fluid on articles disposed in the corners of movable rack assembly 100, as compared to systems known heretofore.

In addition, fluid in cavity 142c is conveyed through spray arm hubs 146 to a respective rotating spray arm assembly 172. As shown in FIG. 8, fluid exiting rotating spray arm assembly 172 forms a spray pattern for spraying fluid on articles disposed on shelves 188. The force of the fluid exiting spray nozzles 182 at the distal ends of rotating spray arm assemblies 172 causes the respective spray arm assembly 172 to rotate about axis 'X.' In this respect, corner spray nozzles 152, in combination with rotatable spray arm assembly 172, provide a system with improved fluid coverage, as compared to systems known heretofore which include only a rotating spray arm.

At the end of the decontamination cycle the flow of pressurized fluid into movable rack assembly 100 ceases. Due to the weight of piston 58 and the lack of pressure within fluid inlet line 22, piston 58 moves downwardly within piston chamber 34a such that piston 58 disengages from first flange 114 of central hub 112. As such, fluid within movable frame assembly 100 is allowed to drain from movable frame assembly 100 through the gap formed between piston 58 and central hub 112.

After a predetermined time, a user is allowed to remove movable rack assembly 100 from chamber 12 of decontamination unit (washer) 10. Because the fluid typically used for the decontamination cycle is hot, the user must take care in removing removable rack assembly 100 from chamber 12. Molded rubber inserts 196 in elongated openings 194 of movable rack assembly 100 allow a user to grasp movable rack assembly 100 within touching the hot metal portions of movable rack assembly 100. Because molded rubber inserts 196 are made of rubber, inserts 196 have less heat capacity, as compared to the metal portions of movable rack assembly 100. Molded rubber elements 196, thus, reduce the risk of a user being burned while removing a hot movable rack assembly 100 from chamber 12 of decontamination unit (washer) 10.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is contemplated that more or fewer corner spray nozzles may be used based on the size of the rack assembly and the desired coverage in the corners of the rack assembly. It is intended that all such modifications and alterations be included insofar as they come within the scope of the invention as claimed or the equivalents thereof.

Having described the invention, the following is claimed:

1. A rack assembly for a washer, comprised of:
   a generally rectangular frame assembly comprised of:
      a central hub connectable to a fluid source;
      a plurality of elongated tubular base members extending from said central hub, said plurality of base members defining a bottom portion of said frame assembly;
      a pair of spaced-apart elongated, tubular side members defining side portions of said frame assembly, said side members lying in planes that are generally parallel to each other, wherein said side members define a space therebetween, said side members having distal ends, each distal end of said side member connected to an end of one of said base members;
      a plurality of spaced-apart transverse members each having a first end connected to one of said side members, wherein said transverse members traverse the space defined between said side members;
      a rotary spray arm attached to each of said transverse members; and
      a plurality of corner spray nozzles on said frame assembly for directing fluid toward corners of said frame assembly;
   vertically spaced-apart, horizontal shelves mounted on said frame assembly, said shelves defining surfaces for supporting articles to be cleaned in said washer; and
   a generally rectangular support frame attached to the bottom portion of said frame assembly, said support frame comprising a plurality of elongated support bar elements that are spaced from the bottom portion of said frame assembly and configured to support the frame assembly,
   wherein a lowermost of the shelves at the bottom portion of said frame assembly has elongated shelf bar elements extending between adjacent ones of said tubular side members, said support frame being attached to said bottom portion of said frame assembly at said shelf bar elements, and
   wherein said base members, said side members and said transverse members are fluidly connected with each other and fluidly connect said rotary spray arms and said corner spray nozzles with said central hub.

2. A rack assembly as defined in claim 1, wherein each of said side members is generally U-shaped, wherein each distal end of said U-shaped side member is connected to an end of a respective base member.

3. A rack assembly as defined in claim 2, wherein said U-shaped side members have spaced-apart leg sections and said transverse member connects one leg section of one U-shaped side section to one leg section of another U-shaped side member.

4. A rack assembly as defined in claim 1, wherein said frame assembly defines a generally rectangular space and the rotary spray arm attached to a respective transverse member is rotatable about a vertical axis through the center of said rectangular space.

5. A rack assembly as defined in claim 1, wherein said transverse members extend diagonally across said rectangular frame.

6. A rack assembly as defined in claim 1, wherein said transverse members are straight tubular members.

7. A rack assembly as defined in claim 1, wherein said base members, said side members and said transverse members are formed of round tubing.

8. A rack assembly as defined in claim 7, wherein said base members, said side members and said transverse members are formed of like round tubing.

9. A rack assembly as defined in claim 1, wherein said shelves are wire racks attached to side members, a shelf being disposed below each rotary spray arm.

10. A rack assembly as defined in claim 1, wherein said frame assembly defines a three-dimensional manifold.

11. A rack assembly as defined in claim 1, wherein said frame assembly is formed of medical grade stainless steel.

12. A rack assembly as defined in claim 1, wherein said support bar elements are spaced from said bottom portion of said frame assembly by spacers extending between said bottom portion of said frame assembly and said support bar elements.

13. A rack assembly as defined in claim 1, wherein said support bar elements are spaced from said shelf bar elements by spacers extending between said shelf bar elements and said support bar elements.

14. A rack assembly for a washer, comprised of:
   a generally rectangular frame assembly comprised of:
      vertically spaced-apart, horizontal shelves mounted on said frame assembly, said shelves defining surfaces for supporting articles to be cleaned in said washer;
      a central hub connectable to a fluid source;
      a plurality of elongated tubular base members extending from said central hub, said plurality of base members defining a bottom portion of said frame assembly;
      first and second spaced-apart elongated, tubular side members defining first and second side portions of said frame assembly, each of said side members comprising a first vertical leg portion, a second vertical leg portion, and a horizontal base portion extending above and between the vertical leg portions, the first and second vertical leg portions extending downwardly from the horizontal base portion, each of the vertical leg portions being attached to an end of one of the tubular base members, said side members defining a space therebetween, the first and second vertical leg portions of the first side member respectively corresponding with the first and second vertical leg portions of the second side member;
      a plurality of spaced-apart transverse members, each of the transverse members extending between the first vertical leg portion of one of the side members and the second vertical leg portion of another one of the side members to traverse the space defined between said side members, each of said transverse members being oriented transverse to an adjacent one of said transverse members and above or below said adjacent transverse member;
      a rotary spray arm attached to each of said transverse members; and
      a plurality of corner spray nozzles, the corner spray nozzles being configured to direct fluid toward corners of said frame assembly, each of said corner spray nozzles being attached to one of said transverse members,
   wherein a lowermost of the shelves at the bottom portion of said frame assembly has elongated shelf bar elements extending between adjacent ones of said tubular side members, said support frame being attached to said bottom portion of said frame assembly at said shelf bar elements, and wherein said base members, said side members and said transverse members are fluidly connected with each other and fluidly connect said rotary spray arms and said corner spray nozzles with said central hub.

15. A rack assembly as defined in claim 14, wherein said frame assembly is further comprised of tubular nipples attached to each of said transverse members, and wherein each of said corner spray nozzles is mounted to one of said tubular nipples.

16. A rack assembly as defined in claim 15, wherein said nozzles are removably mounted to said nipples.

17. A rack assembly for a washer, comprised of:

a generally rectangular frame assembly comprised of:
   a central hub connectable to a fluid source;
   a plurality of elongated tubular base members extending from said central hub, said base member defining a bottom portion of said frame assembly;
   a vertical member extending upwardly from a distal end of each of said plurality of elongated tubular base members, said vertical members and said base members defining an interior space of said frame assembly; and
   a plurality of spaced-apart transverse members having ends connected respectively to said vertical members, wherein said transverse members traverse said interior space of said frame assembly;

a rotary spray arm attached to each of said transverse members;

a generally rectangular support frame attached to the bottom portion of said frame assembly, said support frame comprising a plurality of elongated support bar elements that are spaced from the bottom portion of said frame assembly and configured to support said frame assembly;

vertically spaced-apart, horizontal shelves mounted on said frame assembly, said shelves defining surfaces for supporting articles to be cleaned in said washer; and a plurality of corner spray nozzles on said frame assembly for directing fluid toward corners of said frame assembly;

wherein a lowermost of the shelves at the bottom portion of said frame assembly has elongated shelf bar elements extending between adjacent ones of said vertical members, said support frame being attached to said bottom portion of said frame assembly at said shelf bar elements, and wherein said bottom members, said vertical members and said traversing members are fluidly connected with each other and fluidly connect said rotary spray arms and said corner spray nozzles with said central hub.

18. A rack assembly as defined in claim 17, wherein at least one of said vertical members defines a corner of said frame.

19. A rack assembly as defined in claim 17, wherein an elongated tubular member connects distal ends of adjacent said vertical members to define a U-shaped side member of said frame.

20. A rack assembly as defined in claim 17, wherein said traversing member extends diagonally across said rectangular frame.

* * * * *